(12) United States Patent
Shaddock et al.

(10) Patent No.: US 7,993,064 B2
(45) Date of Patent: Aug. 9, 2011

(54) PHOTONIC POWER DEVICES AND METHODS OF MANUFACTURING THE SAME

(75) Inventors: David Mulford Shaddock, Troy, NY (US); Christopher James Kapusta, Delanson, NY (US); Glen Peter Koste, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 137 days.

(21) Appl. No.: 12/060,430

(22) Filed: Apr. 1, 2008

(65) Prior Publication Data

US 2009/0245735 A1    Oct. 1, 2009

(51) Int. Cl.
*G02B 6/36*    (2006.01)

(52) U.S. Cl. ............. 385/92; 385/88; 385/93; 385/94

(58) Field of Classification Search ............. 385/88–94; 438/118; 257/E21.505
See application file for complete search history.

(56) References Cited

U.S. PATENT DOCUMENTS

| | | | | |
|---|---|---|---|---|
| 4,186,996 A | * | 2/1980 | Bowen et al. ............. | 385/92 |
| 5,011,247 A | * | 4/1991 | Boudreau et al. ......... | 385/33 |
| 5,257,336 A | * | 10/1993 | Dautartas ................... | 385/93 |
| 5,307,435 A | * | 4/1994 | Chihara ..................... | 385/92 |
| 5,337,398 A | * | 8/1994 | Benzoni et al. ............ | 385/90 |
| 5,537,503 A | * | 7/1996 | Tojo et al. ................. | 385/93 |
| 5,546,490 A | * | 8/1996 | Kikuchi et al. ............ | 385/93 |
| 5,647,044 A | * | 7/1997 | Basavanhally et al. ..... | 385/92 |
| 5,684,903 A | * | 11/1997 | Kyomasu et al. .......... | 385/93 |
| 6,748,143 B2 | * | 6/2004 | Kuhara et al. ............. | 385/49 |
| 7,066,660 B2 | * | 6/2006 | Ellison ...................... | 385/92 |
| 7,438,479 B2 | * | 10/2008 | Mitamura .................. | 385/78 |
| 7,762,730 B2 | * | 7/2010 | Kihara et al. .............. | 385/92 |
| 2003/0188646 A1 | * | 10/2003 | Miyahara et al. .......... | 101/129 |
| 2004/0240803 A1 | * | 12/2004 | Rechberger et al. ....... | 385/93 |
| 2006/0140534 A1 | * | 6/2006 | Liu et al. ................... | 385/14 |
| 2007/0081770 A1 | * | 4/2007 | Fisher ........................ | 385/92 |
| 2007/0140624 A1 | * | 6/2007 | Wipiejewski .............. | 385/88 |
| 2008/0145060 A1 | * | 6/2008 | Nelson et al. .............. | 398/135 |

OTHER PUBLICATIONS

CYOPTICS, "TO293BU-XYZ 1310nm DFB Laser Diode in TO-can package for use in Uncooled applications up to 2.7Gb/sec", Data Sheet Jan. 2007, pp. 1-6, www.cyotics.com.

* cited by examiner

*Primary Examiner* — Ellen Kim
(74) *Attorney, Agent, or Firm* — Richard A. DeCristofaro

(57) ABSTRACT

A high temperature optoelectronic device package includes a substrate, an optoelectronic die situated on an upper surface of the substrate, a seal surrounding the optoelectronic die and situated on the upper surface of the substrate and a housing disposed on the seal having a ferrule-seating portion. The housing is disposed on the seal such that a fiber optic center of the ferrule-seating portion is aligned with an active portion of the optoelectronic die. The optoelectronic die is in operative communication with electronic traces of the substrate.

15 Claims, 7 Drawing Sheets

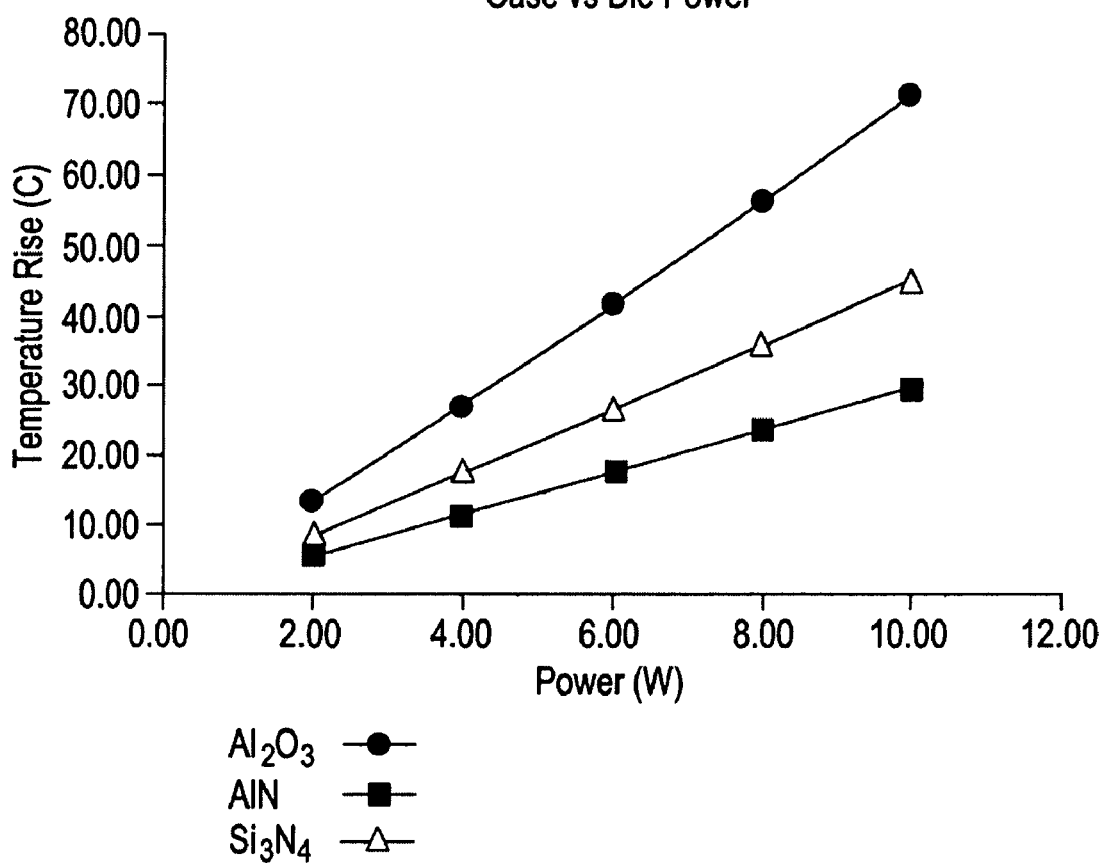

PHOTONIC POWER DEVICES AND METHODS OF MANUFACTURING THE SAME

CROSS REFERENCE TO RELATED APPLICATIONS

The U.S. Government may have certain rights in this invention pursuant to contract number F33615-03-D-2352 DO 0011 awarded by the Air Force Research Laboratory, Wright-Patterson Air Force Base, Ohio.

BACKGROUND OF THE INVENTION

Embodiments of the invention generally relate to photonic power devices, and more particularly to high temperature photonic power devices and methods of manufacturing the same.

Generally, optoelectronic devices convert optical energy into electrical energy (or vice versa). In some applications, optical energy, or light, is coupled to optical fiber and dispersed over a receptive surface of an optoelectronic device. Photons of the light excite electrons within the optoelectronic device, promoting said electrons across a band-gap, and produce a net difference or voltage in the optoelectronic device. This net difference is the output electrical energy.

However, several issues arise in real world application of fiber-coupled light transmission systems. For example, in both single-mode and multimode optical fiber systems it is difficult to properly align light output from the optical fiber to efficiently disperse light onto a surface of an optoelectronic device of an optoelectronic device package. In some fiber-coupled systems light sources must be active during alignment and active measurements must be taken from an output of the optoelectronic device (i.e., active alignment). Active alignment procedures such as this add significant cost and time to the manufacturing process.

Furthermore, thermal issues may arise within and around the optoelectronic device during operation and active alignment. As most optoelectronic devices are semiconductor-based devices, thermal changes during operation must be taken into account to ensure efficient and/or maximum output. For example, increased heat may cause alteration of the nominal profile of a semiconductor's band-gap, thereby decreasing the efficiency in collection of photons due to a change in the responsive frequency of photon absorption within the widened band-gap.

Moreover, in high-power applications (i.e., high-wattage light applications) these issues become exceedingly problematic. For example, overall temperature limits of general devices may reach only about eighty-five degrees C. and may have very high temperature differences between the actual semiconductor die and a case mounting the die. The temperature differences during operation may lead to further stress if the temperature threshold is breached, resulting in less efficiency or causing malfunction or even destruction of the device. The temperature differences may be a result of several bonding surfaces and/or interfaces, and may result in increased thermal resistance of the entire package (i.e., optoelectronic device and die).

Therefore, example embodiments of the present invention provide high temperature photonic power devices.

BRIEF DESCRIPTION OF THE INVENTION

An embodiment of the invention includes a high temperature optoelectronic device package. A high temperature optoelectronic device package includes a substrate, an optoelectronic die situated on an upper surface of the substrate, a seal surrounding the optoelectronic die and situated on the upper surface of the substrate and a housing disposed on the seal having a ferrule-seating portion. The housing is disposed on the seal such that a fiber optic center of the ferrule-seating portion is aligned with an active portion of the optoelectronic die. The optoelectronic die is in operative communication with electronic traces of the ceramic substrate.

Another embodiment of the invention includes a method of manufacturing a high temperature optoelectronic device package. The method includes patterning electrodes and glazing a seal on a substrate, attaching an optoelectronic device die on the substrate, and aligning a receptacle with the optoelectronic device die on the substrate to form the optoelectronic device package.

BRIEF DESCRIPTION OF THE DRAWINGS

These and other features, aspects, and advantages of the present invention will become better understood as the following detailed description is read with reference to the accompanying drawings in which like reference numerals represent like elements throughout the drawings, wherein:

FIG. 7 is a graph depicting modeled temperature results from high temperature optoelectronic device package using different substrate materials.

DETAILED DESCRIPTION OF THE INVENTION

Figure 1:
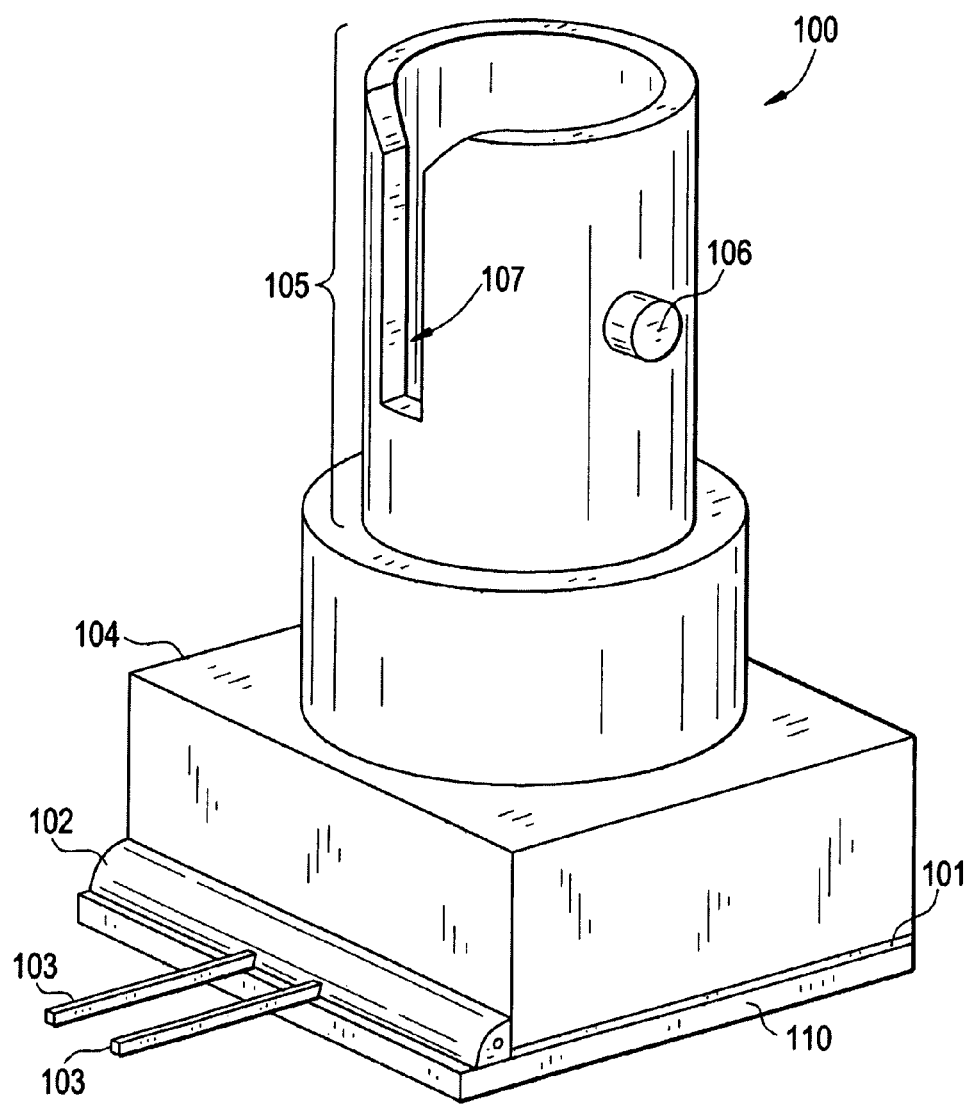
FIG. 1 illustrates a high temperature optoelectronic device package, according to an example embodiment.

Detailed illustrative embodiments are disclosed herein. However, specific functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments.

It will be understood that, although the terms first, second, etc. may be used herein to describe various steps or calculations, these steps or calculations should not be limited by these terms. These terms are only used to distinguish one step or calculation from another. For example, a first calculation could be termed a second calculation, and, similarly, a second step could be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting of example embodiments.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Hereinafter, example embodiments of the present invention will be described in detail. According to example embodiments, high temperature optical devices (i.e., packages) and passive alignment packaging methods are disclosed. The package may provide an efficient means to couple an optical fiber to a photovoltaic or photodiode device (i.e., optoelectronic device). The package supports high temperatures and has low thermal resistance between die and case. The passive alignment packaging method may allow for passive alignment of the optical fiber to the device, thereby simplifying an assembly process.

According to an example embodiment, the package consists of a patterned high thermal conductivity substrate on which an optoelectronic device is mounted and electrically connected with wire or ribbon bonds. The package is interfaced with an optical connector aligned to the die via the package design. The die is sealed from the external environment with a glass seal and optical window for transmission. One example application of the high temperature optical package is for coupling a multimode fiber connector to a relatively large area (>1 mm$^2$) photovoltaic cell for delivering electrical power over fiber. In a single-mode fiber application, this area may be relatively smaller. This example application may be useful for delivering electrical power over fiber where the electronics being powered by the device are at high temperature and are located in a high electromagnetic interference (EMI) environment or at high electrical potential.

Turning to FIG. 1, high temperature optoelectronic device package 100 is illustrated. Package 100 includes a substrate 110. The substrate 110 may comprise a variety of materials. For example, the substrate may be an aluminum oxide substrate, an aluminum nitride substrate, a beryllium oxide substrate, a silicon nitride substrate, a direct-bond copper substrate, and/or any suitable substrate including multi-layer metal and/or ceramic substrate materials.

The package 100 further includes seal 101 formed above the substrate 110. The seal may be silica or solder based, and may form a hermetic seal between the substrate 110 and the housing 104 disposed above the seal 101. The seal may also be borosilicate based, or any other suitable glass seal or solder seal may be used.

The housing 104 is a relatively cylindrical housing, with a generally square bottom portion (disposed in direct contact with the seal 101) and a more generally cylindrical upper portion disposed above the bottom portion. The housing 104 may be composed of a metallic alloy designed to have thermal conductivity and/or expansion characteristics similar to the seal and/or substrate. For example, if borosilicate or silica based glass sealant is used for seal 101, a suitable metallic alloy for housing 104 may be a nickel cobalt ferrous alloy. However, example embodiments should not be limited to only ferrous alloys, or this particular nickel cobalt iteration. Any alloy yielding thermal conductivity and/or expansion characteristics in line with the seal and/or substrate used is intended to be within the scope of example embodiments. Furthermore, although the housing 104 is illustrated as being generally cylindrical, it should not be limited to only cylindrical shapes. For example, a generally rectangular shaped housing may be used depending upon any particular implementation.

The package 100 further includes an electrical insulation, encapsulation, and/or potting portion 102 disposed across a corner formed between the housing 104 and the substrate 110. The encapsulation portion 102 may be comprised of virtually any electrically insulating material with the ability to reach a temperature threshold within a desired range for the end product or packaged device. For example, if the device is intended to operate at 150 degree C., the encapsulation portion 102 should be rated to reach 150 degrees C. (this is given by way of example only, and is not limiting).

The package 100 further includes electrical leads 103. The electrical leads 103 may be in electrical contact with an optoelectronic device within the housing 104, and may be comprised of virtually any electrical conductor.

The interior of upper portion of housing 104 may be shaped or fashioned to accommodate a general connector, for example, a fiber optic ferrule connector. The exterior of upper portion of housing 104 may be shaped or fashioned to accommodate a general receptacle, for example, a ST receptacle (i.e., see portion 105). In a ST receptacle, two peg-like prongs 106 protrude from either side of the housing 104, and a rectangular slot 107, open at an upper surface of the housing 105, exists at one side of the housing 104.

Figure 2:
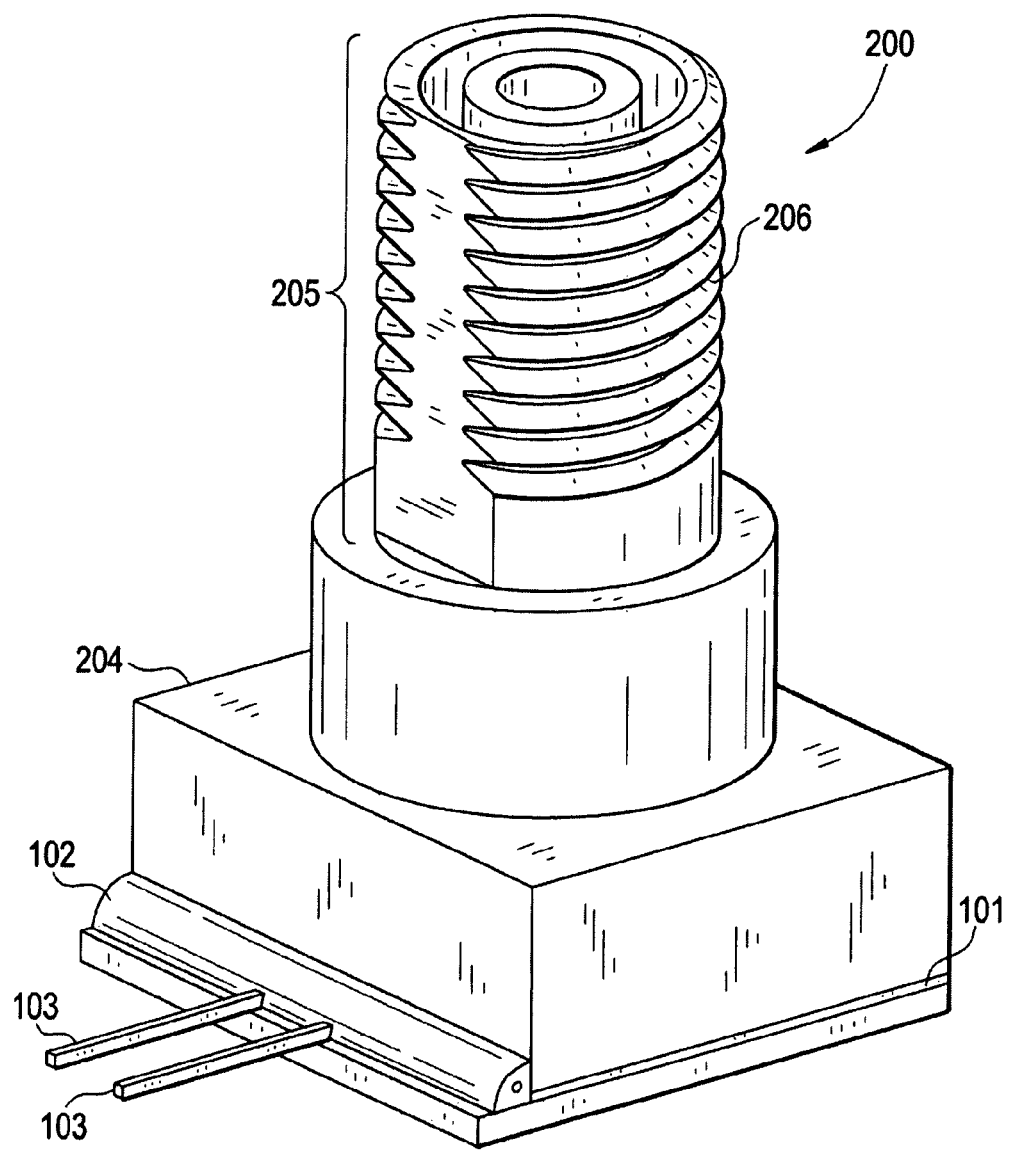
FIG. 2 illustrates a high temperature optoelectronic device package, according to an example embodiment.

FIG. 1 depicts upper portion of housing 104 shaped as a ST receptacle for example only, as the upper portion 105 may be shaped as any receptacle. Turning to FIG. 2, a housing 204 is illustrated with a threaded receptacle such as an FC or SMA receptacle. The threads 206 allow a ferule with a threaded connector to be mechanically joined with the housing 204 with relatively little difficulty. However, it is noted that example embodiments should not be limited to only ST receptacles and threaded receptacles as any receptacle allowing for relatively easy mechanical joining of the housing portion and a fiber optic ferule connector should be considered within the scope of example embodiments, such as MTP, SC, LC receptacles, or rectangular receptacles.

Figure 3:
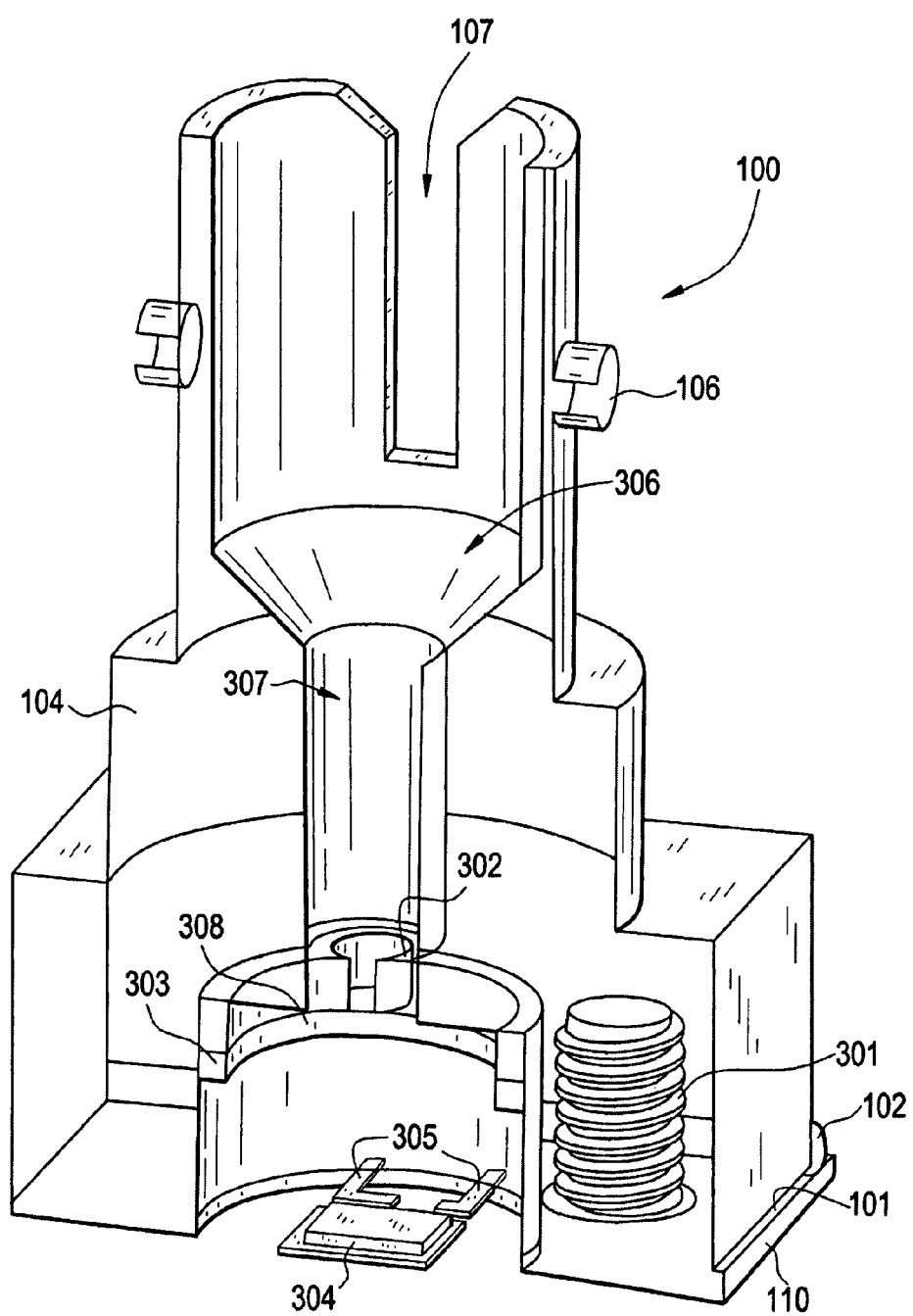
FIG. 3 is a cross section of a high temperature optoelectronic device package, according to an example embodiment.

Turning to FIG. 3, a cross section of a high temperature optoelectronic device package is illustrated. As shown, housing 104 is a structure formed from one piece of the metallic alloy. More clearly, the housing 104 is a contiguous structure of the metallic alloy. The interior of the upper portion of the housing 104 includes a conical portion 306 and a ferrule-engaging portion 307. The conical portion 306 may act as a guide during connection or disconnection of the housing 104 and a connector, such that a ferrule of the connector is guided into the ferrule-engaging portion 307. The ferrule-engaging portion 307 has a generally cylindrical shape, and provides a secure structure for support of a ferrule.

The housing 104 further includes a ferrule-seating portion 302. The ferrule-seating portion 302 is positioned in operative contact with the ferrule-engaging portion 307, at the base of the ferrule-engaging portion 307. Therefore, if a ferrule is inserted in the housing 104, the ferrule may be seated against the ferrule-seating portion 302, and be supported by the ferrule-engaging portion 307.

The housing 104 further includes an optical window 308. The optical window 308 is directly beneath the ferrule-seating portion 302. The optical window 308 may be a glass, quartz or sapphire window, but other suitable materials are also applicable to example embodiments. The optical window 308 may allow photons exiting an optical fiber housed in a ferrule seated against ferrule-seating portion 302 to be dispersed onto an optoelectronic device. The optical window may also be configured as a lens to condition the light for optimal illumination the optoelectronic device die. It is noted however, that according to at least one example embodiment, the optical window 308 may be omitted entirely. For example, if hermeticity is not desired within the housing, a window may not be necessary and/or desired, further simplifying the optoelectronic package.

The housing 104 further includes pre-form 303. The pre-form 303 is seated against the window 308 and the housing 104. Therefore, the pre-form, if allowed to re-flow, or melt and cool, would form a sealed structure supporting the window 308 against the ferrule seating-portion 302 within the housing 104. The pre-form 303 may re-flow using a variety of heating methods. For example, re-flow ovens exist which can accurately control heating and cooling using radiation, convection, etc. Further, the entire housing 104 may be placed on a heating plate or other apparatus to heat the housing 104 until the pre-form 303 re-flows. It is also noted that the perform 303 may be comprised of any suitable material allowing a sealed connection between the window 308 and the ferrule-seating portion 302. For example, glass or glass-like materials may be used, or solder and/or solder-brazing materials may also be used.

Turning back to FIG. 3, an optoelectronic device die 304 is illustrated disposed on the upper surface of the substrate 110. Electric leads, lead wires, or lead traces 305 are also present on the upper surface of the substrate 110, and are in operative contact with the optoelectronic die 304. Alternatively, for example if a multi-layered substrate is used, the traces 305 may be present within the substrate 110. Furthermore, a plurality of planar levels of traces may be used to allow for more complex connections to the optoelectronic die 304. Vias or inter-planar conductive holes may be used to allow interconnection at the upper or lower surface of the substrate 110. Furthermore, there may be wire bonds in place between the traces and the optoelectronic die 304. Therefore, electrical energy created from photons dispersed on the optoelectronic die 304 may be transferred outside the housing 104 through the traces 305.

The high power optoelectronic package further includes a threaded portion 301 to aid in securing and/or affixing the substrate 110 to a heat sink. For example, a threaded screw or bolt may be inserted into threaded portion 301 and be torqued or tightened to a desired specification to apply pressure between the substrate 110 and a heat sink with a thermal interface material there-between. It is noted that although not illustrated, a second threaded portion may also be included opposite to the threaded portion 301 to ensure proper security of the substrate 110. Hereinafter, a method of producing a high power optoelectronic device package will be described with reference to FIGS. 4 and 5.

Figure 4:
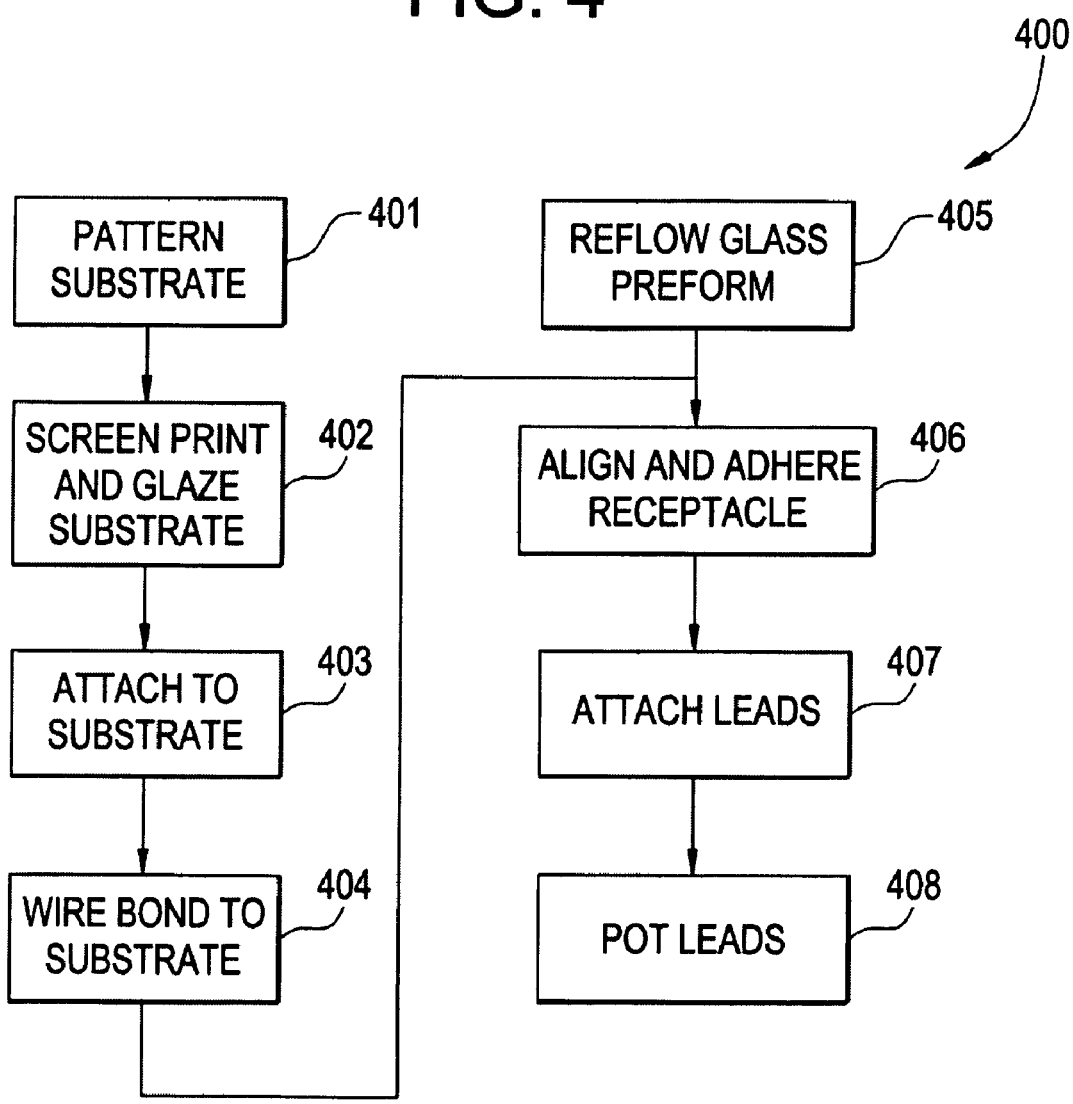
FIG. 4 is a flow chart of a method of producing a high temperature optoelectronic device package, according to an example embodiment.

FIG. 4 is a flow chart of a method of producing a high temperature optoelectronic device package, according to an example embodiment. As illustrated, the method 400 includes patterning a substrate at block 401. The substrate may be a substrate somewhat similar to substrate 110. The substrate may be patterned to include electrical traces, die mount alignment markings, and/or any other suitable patterns. Furthermore, as noted above, the traces may be within the substrate for example, if a multi-layered substrate is used. The method 400 further includes depositing and firing a paste at block 402 (e.g., screen printing and glaze firing the paste). The deposited paste may be suitable for attaching a receptacle to the substrate. The paste may be glass based, solder based, or may comprise any suitable material for attaching receptacle to the substrate.

The method 400 further includes attaching the optoelectronic die to the substrate at block 403. For example, an optoelectronic source or receiver may be placed or attached using a thermally conductive adhesive, solder, or other bonding material. Further, the method 400 includes wire bonding or ribbon bonding the optoelectronic die to the substrate at block 404. For example, conductive bonds may be led from the optoelectronic die to the electronic traces patterned at block 401.

The method 400 further includes reflowing a pre-form to secure the optical window at block 405. The pre-form may be somewhat similar to the pre-form 303, and thus detailed description will be omitted for the sake of brevity. However, it is noted that block 405 may occur in parallel with any of blocks 401, 402, 403, and 404 without departing from the scope of example embodiments. Further, block 405 may be omitted entirely if a window has been previously affixed to a housing 104.

Turning back to FIG. 4, the method 400 further includes aligning and attaching the receptacle to the die at block 406. For example, this may be a passive alignment process. The receptacle may be a housing somewhat similar to housing 104 or 204, shaped or formed to be a receptacle or to accept a general connector. The receptacle may be situated above the substrate, and the optoelectronic die may be identified below the receptacle. Through careful examination of the position of the die, the receptacle may be placed on the substrate such that the optoelectronic die is situated directly beneath the ferrule-seating portion of the receptacle. In this manner, photons from fiber optic cable within a ferrule will be efficiently dispersed on the optoelectronic die. Once properly aligned a sealant layer (e.g., the paste noted above) may be reflowed to attach the receptacle to the substrate.

The method 400 further includes attaching leads at block 407. For example, metallic or conductive leads relatively larger and/or stronger that the traces may be attached to the traces. Thereafter, the leads may be encapsulated at block 408, for example, the leads may be potted.

Figure 5:
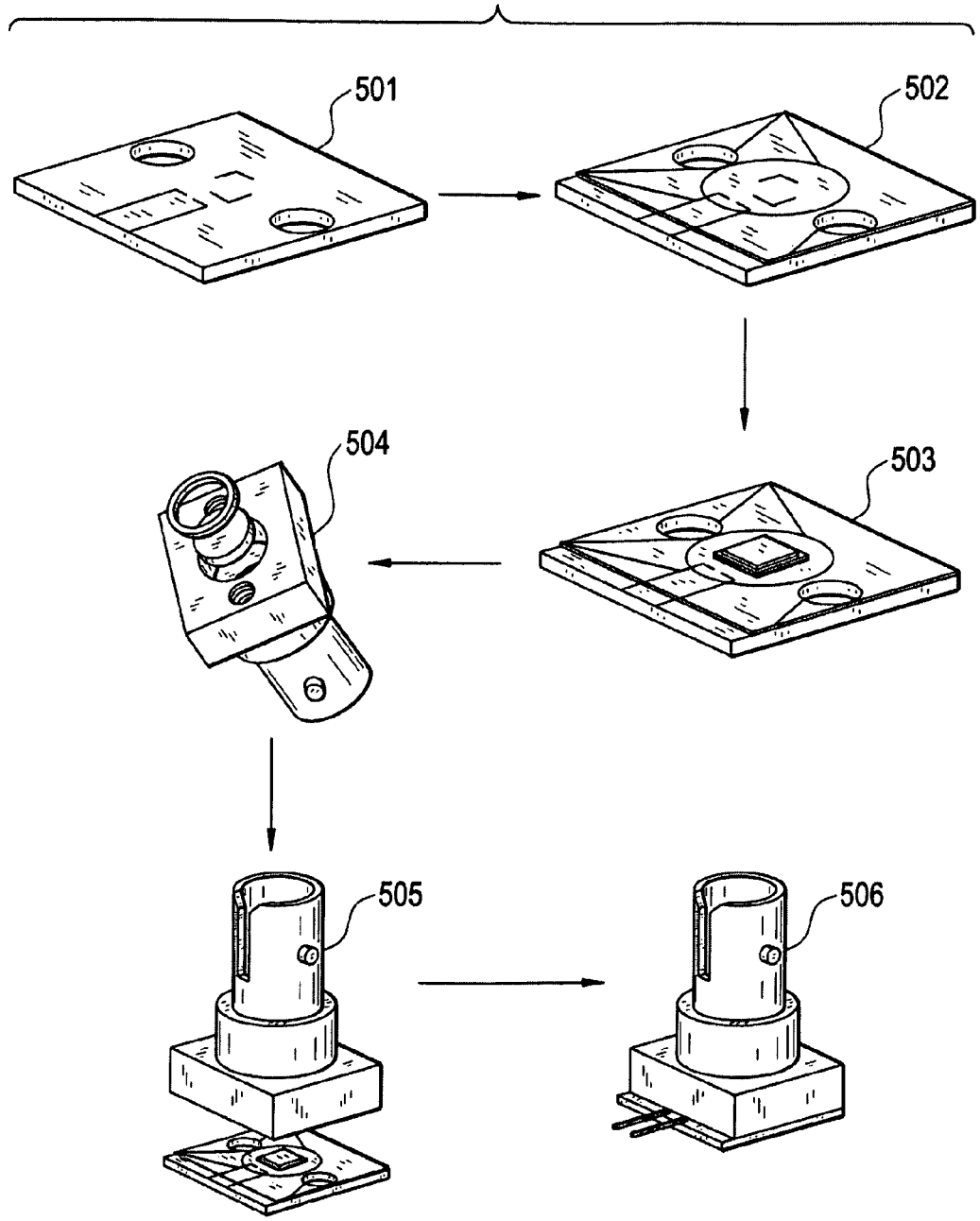
FIG. 5 is a pictorial diagram of a method of producing a high temperature optoelectronic device package, according to an example embodiment.

FIG. 5 is a pictorial diagram of a method of producing a high temperature optoelectronic device package, according to an example embodiment. FIG. 5 further describes portions of the method of FIG. 4 to aid in gaining further understanding of example embodiments. As illustrated, the method includes patterning the substrate at diagram 501. The method further includes depositing and firing a paste on the substrate at diagram 502 (e.g., screen printing and glaze firing the paste). The method further includes attaching the die to the substrate at diagram 503 and ribbon bonding or wire-bonding the die (not shown) to the conductive traces. The method further includes reflowing the pre-form at diagram 504. The method further includes aligning the receptacle to the optoelectronic die at diagram 505 and sealing the receptacle to the substrate. The method further includes attaching leads and encapsulating the leads at diagram 506. For example, the leads may be potted.

Figure 6:
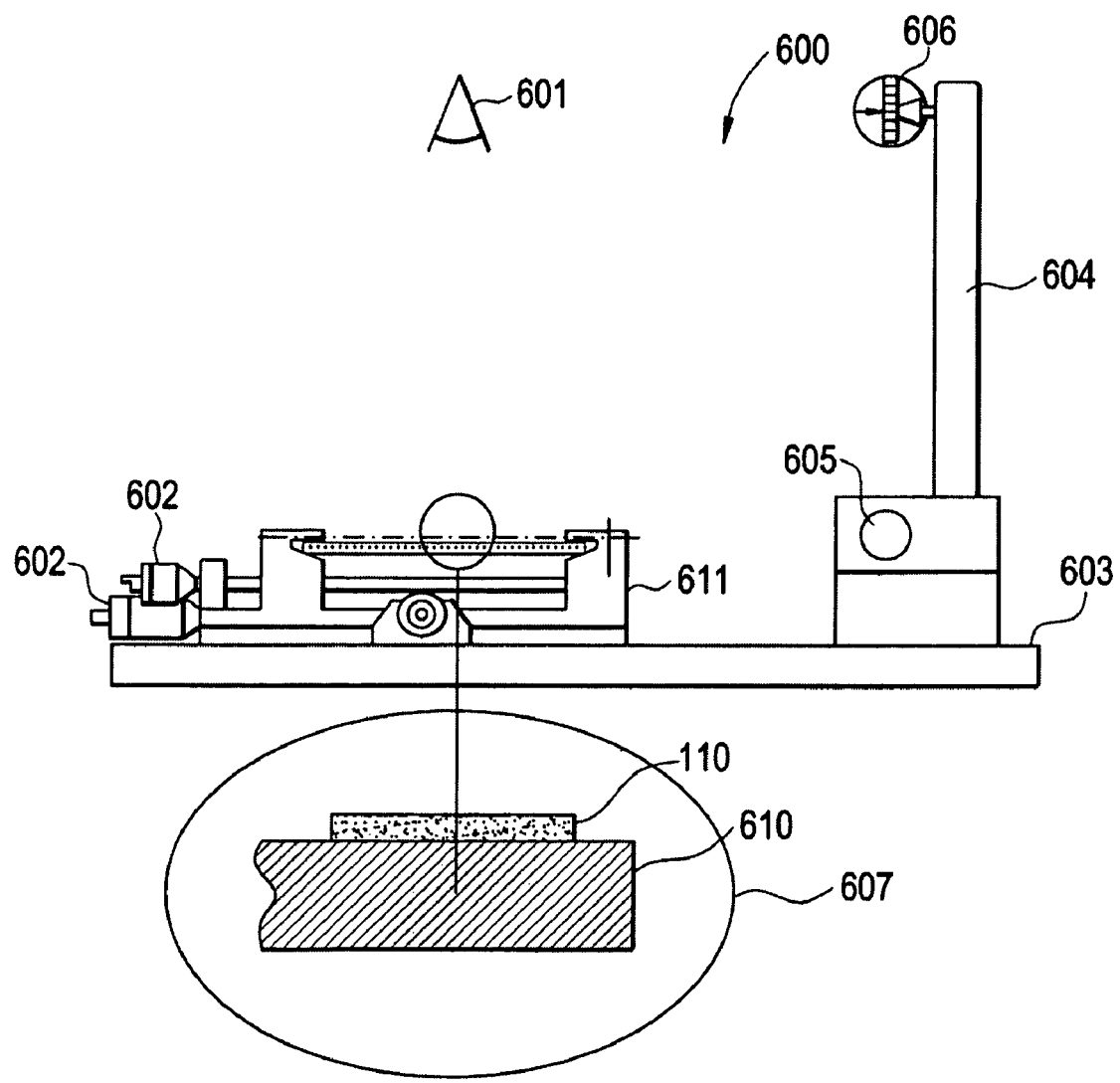
FIG. 6 is an example system for passive alignment of a high temperature optoelectronic device package, according to an example embodiment.

FIG. 6 is an example system for passive alignment of a high temperature optoelectronic device package, according to an example embodiment. The example system may be used in, for example, block 406 of FIG. 4 and diagram 505 of FIG. 5.

The system 600 includes an observation point 601. The observation point 601 may be a microscope or camera, and may allow for passive alignment of an optoelectronic die and receptacle with no or minimal performance penalty. Passive alignment refers to aligning the receptacle and the substrate without applying optical or electrical power to the optoelectronic device die during the alignment process. The system includes translation stages 611 and translation table/stage 610 (see extrapolated section 607), where substrate 110 may be placed. The substrate should have an optoelectronic die affixed to the upper surface before alignment. Course and fine adjustment knobs 602 may be used, with the aid of observation point 601, to align the substrate 110 and the optoelectronic die thereon, with a receptacle on receptacle securing portion 606. The system 600 may further include a prism or partially reflecting mirror (not illustrated) to allow simultaneous observation of the ceramic substrate 110 and receptacle-securing portion 606 for alignment. The prism or partially reflecting mirror may be positioned such that the observation point 601 may observe the receptacle securing portion 606 and the substrate 110. The receptacle-securing portion 606 may be lowered over the ceramic substrate using pivot point 605, and after proper alignment, the receptacle (or the entire stage) may be heated to reflow a seal (e.g., seal 101 of FIGS. 1-3).

FIG. 7 is a graph depicting modeled temperature results from high temperature optoelectronic device package. Because of the contiguous nature of the substrate 110, and the decreased number of interfaces between the substrate and the optoelectronic device die 304, decreased thermal resistance of the entire package has been achieved. The temperature profile of the high power optoelectronic package has been modeled to determine performance using a variety of substrate materials. FIG. 7 depicts die to case temperature rise vs. die power for ceramic comprised of aluminum oxide, aluminum nitride, and silicon nitride as examples only.

With only some example embodiments of the present invention having thus been described, it will be obvious that the same may be varied in many ways. The description of the invention hereinbefore uses these examples, including the best mode, to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Such variations are not to be regarded as a departure from the spirit and scope of the present invention, and all such modifications are intended to be included within the scope of the present invention as stated in the following claims.

What is claimed is:

1. A high temperature optoelectronic device package, comprising:
   a substrate;
   an optoelectronic die situated on an upper surface of the substrate, the optoelectronic die being in operative communication with electronic traces of the substrate;
   a seal disposed on an uppermost surface and about a perimeter of the substrate and surrounding the optoelectronic die; and
   a one-piece housing disposed on the seal and having integrally formed therein;
   a ferrule-seating portion;
   a window disposed below the ferrule-seating portion and above the optoelectronic die, wherein the window is formed of an optically transparent material and wherein the window is not coupled to the substrate;
   a pre-form disposed between the window and the ferrule-seating portion, wherein the preform physically supports the window against the ferrule-seating portion;
   a cylindrical ferrule-engaging portion disposed above the ferrule-seating portion; and
   a conical ferrule-alignment portion disposed above the ferrule-engaging portion,
   the housing disposed on the seal such that a fiber optic center of the ferrule-seating portion is aligned with an active portion of the optoelectronic die.

2. The package of claim 1, further comprising at least one threaded hole perpendicular to the substrate and penetrating the substrate.

3. The package of claim 1, further comprising electric leads in operative communication with the electronic traces, wherein the electronic leads are disposed on an outer portion of the housing.

4. The package of claim 1, wherein:
   an upper portion of the housing is configured to receive a non-threaded connector including a fiber-optic ferrule.

5. The package of claim 1, wherein:
   an upper portion of the housing is configured to receive a threaded connector including a fiber-optic ferrule.

6. The package of claim 1, wherein the window is a lens.

7. The package of claim 1, further comprising a pre-form disposed between the window and the housing, physically supporting the window against the ferrule-seating portion.

8. The package of claim 1, wherein the substrate is one of an aluminum oxide substrate, an aluminum nitride substrate, a beryllium oxide substrate, a silicon nitride substrate, a multi-layered substrate, and a direct-bond copper substrate.

9. The package of claim 1, wherein the housing is composed of a metallic alloy.

10. The package of claim 9, wherein the metallic alloy is a nickel cobalt ferrous alloy.

11. A method of manufacturing a high temperature optoelectronic device package, comprising:
   patterning a substrate;
   depositing and firing a paste on an uppermost surface of the substrate;
   attaching an optoelectronic device die to the substrate;
   reflowing a pre-form to secure a window below a ferrule-seating portion and above the optoelectronic die of the optoelectronic device package, wherein the preform physically supports the window against the ferrule-seating portion and wherein the window is not coupled to the substrate;
   aligning the receptacle with the optoelectronic device die on the substrate to form the optoelectronic device package; and
   reflowing the deposited paste to attach the receptacle to the substrate and form a seal between the receptacle and a perimeter of the uppermost surface of the substrate.

12. The method of claim 11, further comprising:
   wire-bonding or ribbon bonding the optoelectronic device die to the substrate.

13. The method of claim 11, further comprising:
   attaching leads to an outer portion of the optoelectronic device portion; and
   encapsulating at least a portion of the leads.

14. The method of claim 11, wherein aligning the receptacle includes passively aligning the receptacle with the optoelectronic device die.

15. The method of claim 11, wherein depositing and firing the paste includes screen-printing and glaze-firing the paste on the substrate.

* * * * *